(12) United States Patent
Nadeau et al.

(10) Patent No.: US 9,687,299 B2
(45) Date of Patent: Jun. 27, 2017

(54) LIGHT REFLECTION AND GLARE PREVENTING MEDICAL INSTRUMENT HOLDING APPARATUS AND RELATED METHODS

(71) Applicant: Symmetry Medical Manufacturing, Inc., Warsaw, IN (US)

(72) Inventors: Russell Nadeau, Greenfield, NH (US); Jason Hawkes, Weare, NH (US); George P. Hannafin, Hudson, NH (US)

(73) Assignee: SYMMETRY MEDICAL MANUFACTURING, INC., Warsaw, IN (US)

(*) Notice: Subject to any disclaimer, the term of this patent is extended or adjusted under 35 U.S.C. 154(b) by 297 days.

(21) Appl. No.: 14/062,159

(22) Filed: Oct. 24, 2013

(65) Prior Publication Data
US 2014/0110288 A1 Apr. 24, 2014

Related U.S. Application Data

(60) Provisional application No. 61/717,942, filed on Oct. 24, 2012.

(51) Int. Cl.
| | |
|---|---|
| A61B 19/02 | (2006.01) |
| A61B 50/20 | (2016.01) |
| A61B 50/33 | (2016.01) |
| A61B 90/90 | (2016.01) |
| A61B 90/94 | (2016.01) |
| A61L 2/26 | (2006.01) |
| A61B 50/00 | (2016.01) |

(52) U.S. Cl.
CPC .......... *A61B 19/0271* (2013.01); *A61B 50/20* (2016.02); *A61B 50/33* (2016.02); *A61B 90/90* (2016.02); *A61B 90/94* (2016.02); *A61B 2050/006* (2016.02); *A61L 2/26* (2013.01); *Y10T 29/49826* (2015.01)

(58) Field of Classification Search
CPC . A61B 19/0271; A61B 19/44; A61B 19/0256; A61B 50/33; A61B 50/30; A61B 50/20; A61B 90/90; A61B 90/94; A61M 5/002
USPC ................................................. 206/363, 370
See application file for complete search history.

(56) References Cited

U.S. PATENT DOCUMENTS

| | | | | |
|---|---|---|---|---|
| 4,626,971 | A | * 12/1986 | Schultz ............ | A61B 17/06061 206/365 |
| 4,637,513 | A | * 1/1987 | Eldrige, Jr. ...... | A61B 17/06161 206/363 |
| 5,281,400 | A | | 1/1994 | Berry, Jr. |
| 5,441,707 | A | | 8/1995 | Lewis et al. |
| 5,628,970 | A | | 5/1997 | Basile et al. |

(Continued)

*Primary Examiner* — Steven A. Reynolds
(74) *Attorney, Agent, or Firm* — Hayes Soloway PC

(57) ABSTRACT

A medical instrument holding apparatus and related methods are disclosed. The apparatus includes a medical instrument container. A medical instrument holding platform is positioned within the medical instrument container, wherein the medical instrument holding platform has a textured surface. At least one marking is positioned on the textured surface. When a quantity of light emitted from a lighting fixture is applied to the textured surface, a reflection from the quantity of light may be prevented.

20 Claims, 6 Drawing Sheets

(56) References Cited

U.S. PATENT DOCUMENTS

| Patent/Publication | Date | Inventor | Classification |
|---|---|---|---|
| 5,848,693 A * | 12/1998 | Davis | A61B 50/33 128/849 |
| 6,048,504 A | 4/2000 | Riley | |
| 6,099,812 A * | 8/2000 | Allen | A61L 2/26 206/370 |
| 6,331,280 B1 | 12/2001 | Wood | |
| 6,379,631 B1 | 4/2002 | Wu | |
| 6,692,693 B2 | 2/2004 | Wu | |
| 6,759,017 B2 | 7/2004 | Wu et al. | |
| 7,309,519 B2 | 12/2007 | Scholz et al. | |
| 7,871,582 B2 | 1/2011 | Riley et al. | |
| 7,965,185 B2 | 6/2011 | Cambre et al. | |
| 2004/0200743 A1 * | 10/2004 | Delaere | G11B 33/045 206/308.1 |
| 2005/0095169 A1 | 5/2005 | Su-Syin | |
| 2005/0137601 A1 * | 6/2005 | Assell | A61B 17/7074 606/79 |
| 2005/0163686 A1 | 7/2005 | Bettenhausen et al. | |
| 2007/0205123 A1 * | 9/2007 | Bettenhausen | A61B 50/34 206/363 |
| 2007/0253864 A1 | 11/2007 | Maguire, Jr. et al. | |
| 2008/0116095 A1 | 5/2008 | Riley et al. | |
| 2008/0159918 A1 | 7/2008 | Wu | |
| 2009/0053103 A1 | 2/2009 | Mortimer et al. | |
| 2010/0012537 A1 * | 1/2010 | Farrar | A61M 5/002 206/364 |
| 2010/0038273 A1 * | 2/2010 | Johnson | B65D 25/34 206/459.5 |
| 2010/0044356 A1 * | 2/2010 | Cope | B23K 26/0876 219/121.67 |
| 2010/0065456 A1 * | 3/2010 | Junk | A61L 2/26 206/363 |
| 2012/0082589 A1 | 4/2012 | Ladison et al. | |
| 2012/0152289 A1 | 6/2012 | Smith et al. | |
| 2012/0152957 A1 | 6/2012 | Smith | |
| 2012/0195792 A1 * | 8/2012 | Duddy | A61L 2/26 422/28 |
| 2014/0083886 A1 * | 3/2014 | Winterrowd | A61B 50/34 206/370 |

* cited by examiner

LIGHT REFLECTION AND GLARE PREVENTING MEDICAL INSTRUMENT HOLDING APPARATUS AND RELATED METHODS

CROSS REFERENCE TO RELATED APPLICATION

This application claims benefit of U.S. Provisional Application Ser. No. 61/717,942 entitled, "Medical Instrument Holding Apparatus with Textured Holding Surface and Related Methods" filed Oct. 24, 2012, the entire disclosure of which is incorporated herein by reference.

FIELD OF THE DISCLOSURE

The present disclosure is generally related to instrument holding devices and more particularly is related to a light reflection and glare preventing medical instrument holding apparatus and related methods.

BACKGROUND OF THE DISCLOSURE

Within the medical industry, there is a need for holding a variety of medical instruments for various purposes. For example, a surgeon needs to be able to access medical instruments for surgery quickly, a dentist needs to be able to access his or her dental tools, and virtually all medical instruments must be placed within a holder during a sterilization process. Conventional holding containers may include a variety of bases holding insertable trays that have specifically-designed areas for holding specific tools. The medical tools may be retained within the insertable trays with supporting structures, such as grommets, brackets, or other devices for retaining the tool. When smaller tools are required to be used, a variety of grommets or holders may be used, or the smaller tools may be grouped in one area. When a surgeon or medical staff member requires a specific tool, he or she must visually identify the appropriate tool within the tray.

After a medical tool is sterilized, it may be capable of being used within a surgical procedure. To prevent contamination, the sterilized medical tools are often left within the trays and sterilization containers until they are needed during the surgical procedure. Surgical procedures almost always utilize very bright and luminous lighting to appropriately illuminate the surgical site. This bright light is necessary for the surgical procedure, since hindering a surgeon's ability to visually comprehend the surgical site may lead to surgical complications having harmful outcomes. The bright lighting, however, not only shines on the surgical site, but also has a tendency to shine on the trays holding the medical instruments needed for the surgical procedure.

The conventionally flat, smooth tray surfaces are commonly manufactured from polyphenylsulphone or a non-corroding metal such as aluminum, stainless steel or titanium, which will reflect the bright surgical light easily. The reflection of light can make it difficult for the surgeon or medical technician to visually identify the location of a specific medical tool, or label corresponding to a specific medical tool. To overcome this problem, surgeons and medical technicians may change their viewing angles or viewing positions relative to the tray, such that the light reflection is diminished enough for them to visually identify the appropriate medical tool or label. However, constantly changing a viewing angle or position is burdensome and can lead to inefficiencies within the surgical procedure.

Thus, a heretofore unaddressed need exists in the industry to address the aforementioned deficiencies and inadequacies.

SUMMARY OF THE DISCLOSURE

Embodiments of the present disclosure provide a medical instrument holding apparatus. Briefly described, in architecture, one embodiment of the apparatus, among others, can be implemented as follows. The medical instrument holding apparatus has a medical instrument container. A medical instrument holding platform is positioned within the medical instrument container, wherein the medical instrument holding platform has a textured surface. At least one marking is positioned on the textured surface.

The present disclosure can also be viewed as providing a method of manufacturing a medical instrument holding apparatus. In this regard, one embodiment of such a method, among others, can be broadly summarized by the following steps: providing a medical instrument container; manufacturing a medical instrument holding platform sized to be positioned within the medical instrument container, wherein the medical instrument holding platform has a textured surface; producing at least one marking proximate to the textured surface; and positioning the medical instrument holding platform within the medical instrument container.

The present disclosure can also be viewed as providing a method of using a medical instrument holding apparatus within a medical operation setting. In this regard, one embodiment of such a method, among others, can be broadly summarized by the following steps: providing a medical instrument container having a medical instrument holding platform positioned therein, wherein at least one medical instrument is positioned within a supporting structure within the medical instrument holding platform; identifying the at least one medical instrument with a marking positioned proximate to a top surface of the medical instrument holding platform, wherein the top surface is a textured surface; illuminating the textured surface of the medical instrument holding platform with at least one lighting fixture; and preventing a glare from a quantity of light emitted from the at least one lighting fixture with the textured surface, thereby allowing the at least one marking to be visually identifiable.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
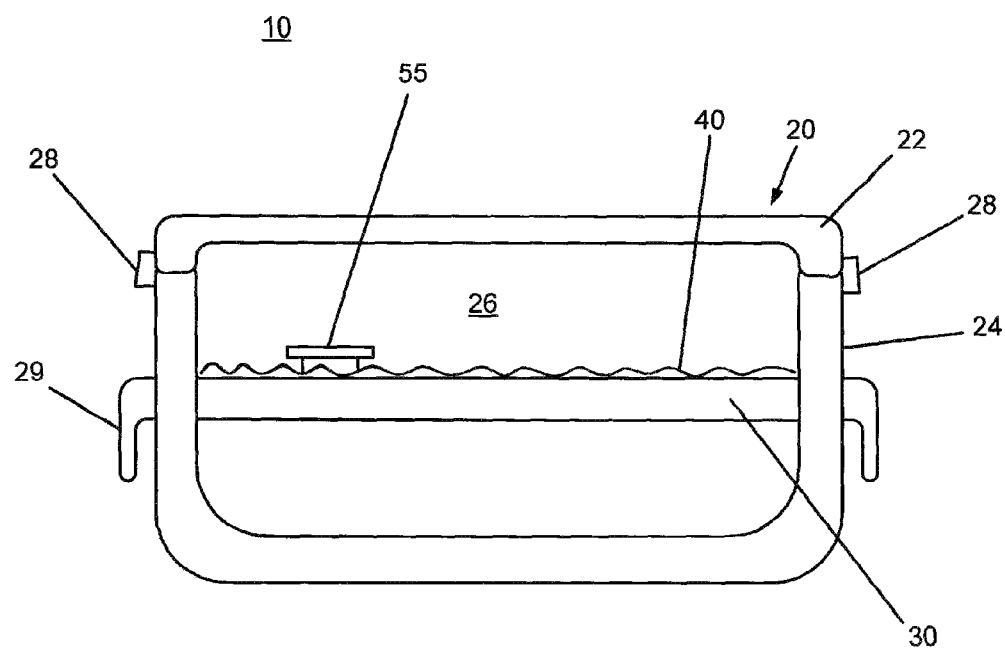
FIG. 1 is a side cross-sectional view illustration of a medical instrument holding apparatus, in accordance with a first exemplary embodiment of the present disclosure.

FIG. 1 is a side cross-sectional view illustration of a medical instrument holding apparatus 10, in accordance with a first exemplary embodiment of the present disclosure. The medical instrument holding apparatus 10, which may be referred to as 'apparatus 10,' includes a medical instrument container 20. A medical instrument holding platform 30 is positioned within the medical instrument container 20, wherein the medical instrument holding platform 30 has a textured surface 40. At least one textual or graphic marking 60 (shown in FIG. 2) is positioned on the textured surface 40.

The apparatus 10 may be used for holding different types of instruments, namely medical instruments used for medical procedures, operations, and surgeries. For example, the apparatus 10 may be used to hold medical instruments in surgical environments before, during and/or after a surgical procedure, or a medical instrument sterilization process. Similarly, the apparatus 10 may be used with dental instruments for dental operations, routine cleanings, or for any other use. Other settings and uses within the medical field are also envisioned, all of which are considered within the scope of the present disclosure. The apparatus 10 is well suited for holding medical instruments during a sterilization process, where the medical instrument is contacted by sterilant or subjected to sterilizing conditions, such as high temperatures.

The medical instrument container 20 may include a variety of different types of containers and container components that can hold a medical instrument. For example, the medical instrument container 20 may include a container base 24 and a container top 22 which can be used to enclose an interior portion 26 of the medical instrument container 20. As is discussed herein, many different configurations are available for the medical instrument container 20. The medical instrument container 20 may be constructed from materials that are capable of withstanding the harsh environments of a sterilization process. These environments generally include high temperatures, moist environments, and chemical sterilant, and therefore durable materials, such as plastics and metal are commonly used to construct the medical instrument container 20. When the medical instrument container 20 is formed from more than one structure, such as when a container base 24 and a container top 22 are used, a container latch 28 may be used to retain the components together. Any number of handles 29 may also be used to provide convenient and safe transport of the medical instrument container 20.

The medical instrument holding platform 30 is positioned within the medical instrument container 20 as a structure that is separate from the medical instrument container 20 or as a structure that is substantially integral with the medical instrument container 20. For example, as is shown in FIG. 1, the medical instrument holding platform 30 is a separate structure that may be positioned within the medical instrument container 20. This separate medical instrument holding platform 30 may be a medical sterilization tray or other structure that holds or retains medical instruments during a sterilization process. As is discussed relative to FIG. 3, the medical instrument holding platform 30 may also be formed integrally with the medical instrument container 20.

The medical instrument holding platform 30 may be permanently affixed to the medical instrument container 20 or removably from the interior portion 26 of the medical instrument container 20. The medical instrument holding platform 30 may have a variety of shapes positioned therein, such as cavities for holding medical instruments 50, perforations in the form of apertures or holes, and any number or type of grommets, brackets, or other medical instrument supporting structures. For example, the apparatus 10 may utilize various structures that contact and hold the medical instrument 50. These structures may be formed from resilient materials, such as a silicone material with a high durometer, such that they can flex to hold a medical instrument successfully. Many common medical instrument supporting structures include permanent or removable rubber or silicon grommets with universal sizing or instrument-specific sizing, or stands that affix to the medical instrument holding platform 30 and hold a medical instrument 50 a distance above the surface of the medical instrument holding platform 30.

The medical instrument holding platform 30 includes a textured surface 40 positioned on at least one side of the medical instrument holding platform 30. The side of the medical instrument holding platform 30 that has the textured surface 40 is the instrument-holding side of the medical instrument holding platform 30, i.e., the side of the medical instrument holding platform 30 that a user will visually see as holding the medical instrument 50. Commonly, the side of the medical instrument holding platform 30 having the textured surface 40 may be facing upwards, such that a user of the apparatus 10 will view the textured surface on the medical instrument holding platform 30 holding the medical instrument(s) 50.

The textured surface 40 may have many different sizes, depths, patterns, or other characteristics, all of which are considered within the scope of the present disclosure. For example, the textured surface 40 may commonly have many small raised points, bumps, ridges, or non-planar structures that prevent the side of the medical instrument holding platform 30 from being completely or substantially smooth. The textured surface 40 may be quantified by a light reflectance value (LRV), as defined in an ASTM standard. It may be preferable for the LRV of the textured surface 40 to be less than 50%, preferably less than 40%, and more preferably, less than 20%. Low reflective and glare conditions may be achieved by the texture, which may be quantified using contact or non-contact profilometry. While the shape and size of the texture on the textured surface 40 may vary, the texture may include, for example, ridges and raised points having a size of 1000 μm or less, more preferably 500 μm or less.

The textured surface 40 may be formed from a variety of methods that either form the medical instrument holding platform 30 with the textured surface 40 therein, or remove material from the medical instrument holding platform 30 to create the textured surface 40. The textured surface 40 is not produced by adding any material, structure, or substance to the side of the medical instrument holding platform 30 after the medical instrument holding platform 30 is produced. For example, paint-on or spray-on additives with an embedded texture-providing material, such as friction-enhancing paints, should not be used. One way to provide the textured surface is to manufacture the medical instrument holding platform 30 by combining at least one platform material, such as polyphenylsulfone, polyetherimide, polysulfone, polyethersulfone, and/or polypropylene, with at least one textural material prior to manufacturing the structure of the medical instrument holding platform 30. Once the medical instrument holding platform 30 is fully formed, the textural material may provide the textured surface 40. Various textural material may be used, including granular materials, fibers such as glass fiber or carbon fiber, or other materials that can produce a texture.

At least one textual or graphic marking 60 (FIG. 2) is positioned on the textured surface 40. The textual or graphic marking 60 may include any type of text, graphic, image, word, picture, or similar marking that is formed within the medical instrument holding platform 30, on top of the medical instrument holding platform 30, or on the textured surface 40. For example, commonly the textual or graphic marking 60 is an ink-based image or word that is formed within the material of the medical instrument holding platform 30. The textual or graphic marking 60 may be positioned proximate to an instrument supporting structure to identify the instrument 50 that the instrument supporting structure is holding or is sized to hold. For example, the marking 60 may be positioned proximate to an instrument supporting structure 55 (FIG. 1) on the medical instrument holding platform 30 to identify a characteristic of a medical instrument (not shown) which is received or positioned within the instrument supporting structure 55. The characteristic of the medical instrument may include an ID, a name, a brand, a size, or other quality of the medical instrument. The textual or graphic marking 60 may also be laser etched on the textured surface 40. Since many medical instruments 50, especially small medical instruments 50, may be difficult to visually distinguish, the use of the textual or graphic marking 60 may be an essential component for identification of the medical instrument 50.

The use of the textured surface 40 on the medical instrument holding platform 30 may provide benefits in allowing the user of the apparatus 10 to visually identify the textual or graphic marking 60 on the medical instrument holding platform 30. The need for the textured surface 40 may arise due to the common use of the apparatus 10 in surgical environments utilizing bright surgical and medical lighting. As such, the lighting has a tendency to reflect off of the upper platform of a medical instrument sterilization tray, thus making it difficult for the user to identify textual or graphical markings positioned on the tray that are used to identify a medical instrument held thereon. Because the user has difficulty in identifying a textual or graphical marking 60 corresponding to an appropriate medical instrument 50, the user may inadvertently select the wrong instrument, or be forced to adjust his or her viewing angle to overcome the light reflection. Accordingly, the use of the textured surface 40 on the medical instrument holding platform 30 may prevent the reflection of light off the surface of the medical instrument holding platform 30, thereby allowing the user to easily view the textual or graphical marking 60 on the medical instrument holding platform 30.

It is noted that while the medical instrument holding platform 30 has a textured surface 40, other components of the apparatus 10 may also have a textured surface. For example, it is envisioned that a base, cover, or other components of the medical instrument container 30 can be formed from a material with an embedded textured component, thereby giving all surfaces of the apparatus 10 a texture. For example, a cover of the apparatus 10 may have a textured surface to prevent reflections and glares from obstructing a surgeon's view of the cover, which may include a label or other identifying information of the apparatus 10.

Figure 2:
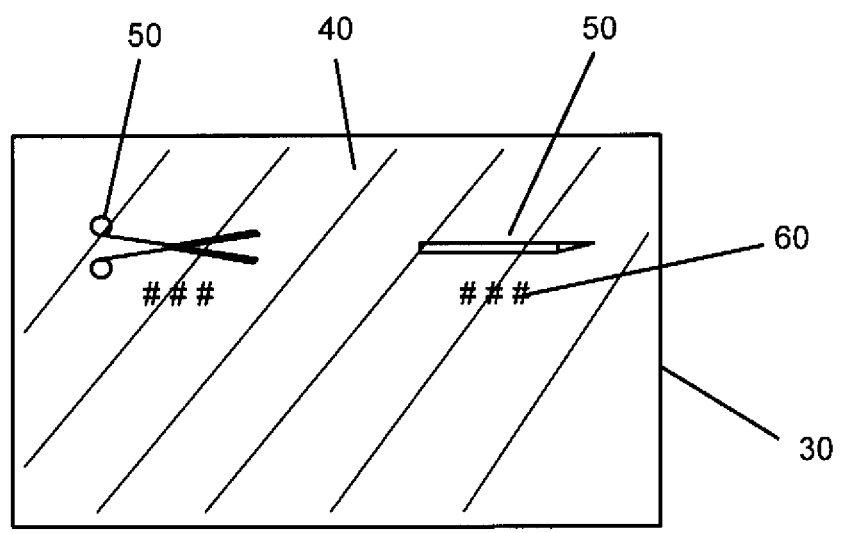
FIG. 2 is a top view illustration of the medical instrument holding platform of the medical instrument holding apparatus of FIG. 1, in accordance with the first exemplary embodiment of the present disclosure.

FIG. 2 is a top view illustration of the medical instrument holding platform 30 of the medical instrument holding apparatus 10 of FIG. 1, in accordance with the first exemplary embodiment of the present disclosure. As can be clearly seen in FIG. 2, the textual or graphical markings 60 may be visibly positioned on the surface of the medical instrument holding platform 30. The textual or graphical markings 60 may be positioned proximate to a location on the medical instrument holding platform 30 where a corresponding medical instrument 50 is positioned, such that the textual or graphical marking 60 provides identification of the medical instrument 50. The textured surface 40 may prevent the reflection of light off of the surface of the medical instrument holding platform 30, which allows for unobstructed viewing of the textual or graphical marking 60. Accordingly, the textured surface 40 allows a user of the apparatus 10 to easily identify a medical instrument 50 when surgical lighting is present by preventing or substantially preventing any reflection, glare, or bright lighting from being transferred by the medical instrument holding platform 30.

Figure 3:
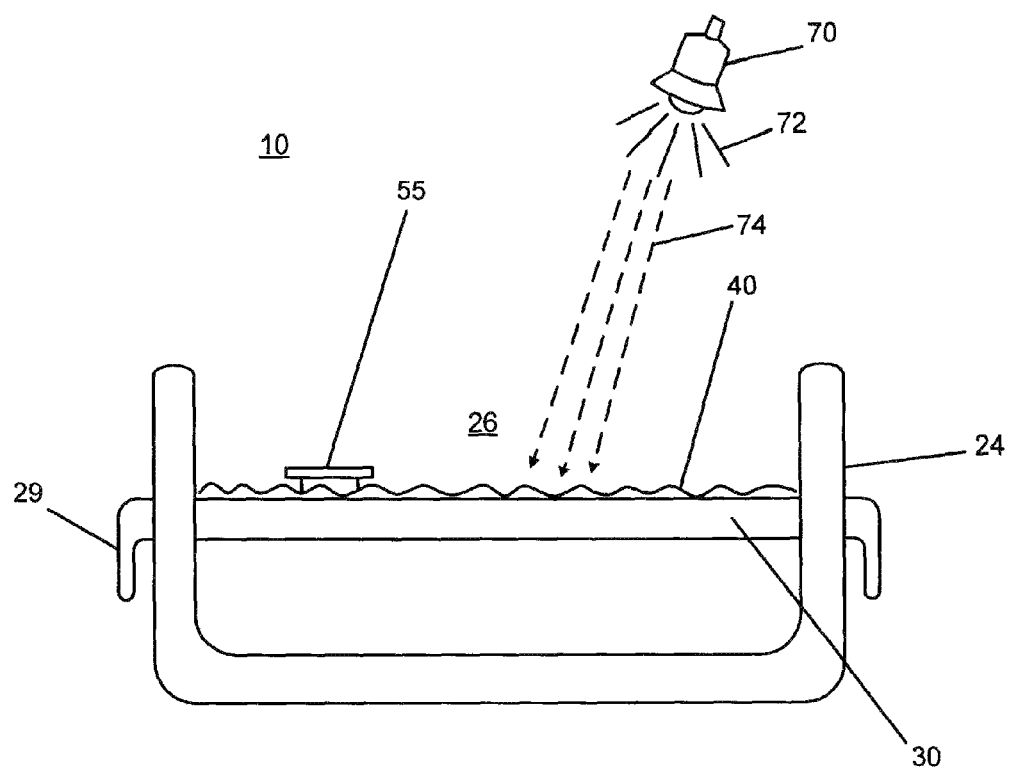
FIG. 3 is a side cross-sectional view illustration of a medical instrument holding apparatus, in accordance with the first exemplary embodiment of the present disclosure.

FIG. 3 is a side cross-sectional view illustration of a medical instrument holding apparatus 10, in accordance with the first exemplary embodiment of the present disclosure. As is shown, the medical instrument holding platform 30 may be used in operational settings that involve the use of lighting fixtures 70. The operational settings may commonly be operating rooms, surgical rooms, emergency rooms, or other medical facilities. The lighting fixtures 70 are often very high power and produce a significant amount of light to provide the doctors and other medical staff with enough lighting to see everything that is needed during a procedure or operation. The lighting fixtures 70 may emit a quantity of light 72 which is directed towards the medical instrument holding platform 30 (indicated by arrows 74). The textured surface 40 of the medical instrument holding platform 30 may prevent the emitted light 74 from reflecting off of the medical instrument holding platform 30 and into the eyes of the doctor or medical staff. In this way, the textured surface 40 may prevent visual impairment of the doctor or medical staff due to the reflection or glare of the emitted light 74, thereby allowing for successful visual identification of the markings 60 (FIG. 2) and the medical instruments.

Figure 4:
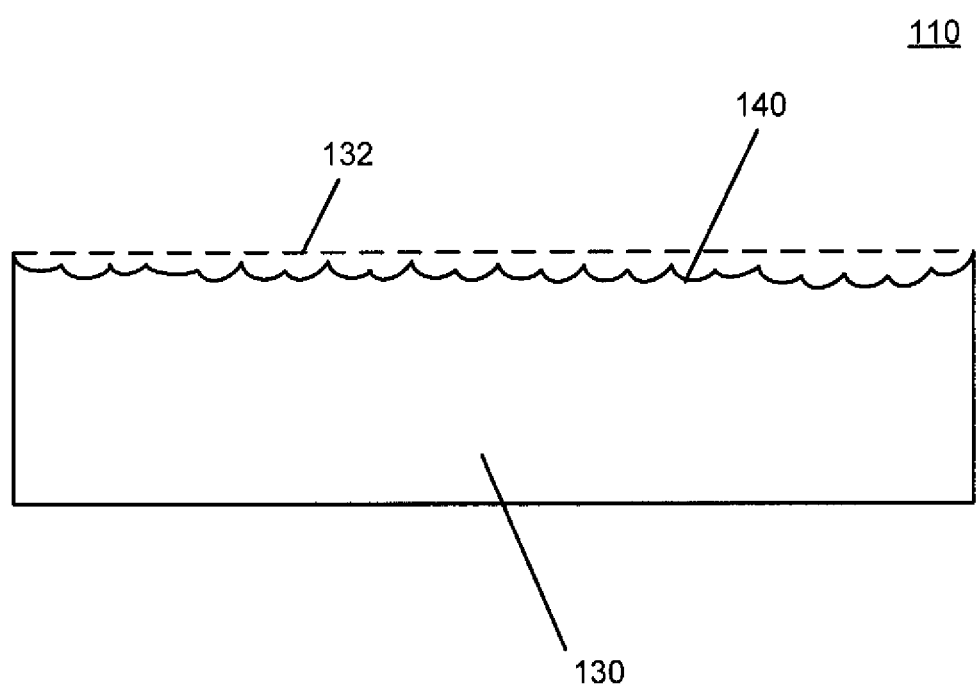
FIG. 4 is a side cross-sectional view illustration of a medical instrument holding platform for use with a medical instrument holding apparatus, in accordance with a second exemplary embodiment of the present disclosure.

FIG. 4 is a side cross-sectional view illustration of a medical instrument holding platform 130 for use with a medical instrument holding apparatus 110, in accordance with a second exemplary embodiment of the present disclosure. The medical instrument holding apparatus 110, which may be referred to as 'apparatus 110,' may be substantially similar to the apparatus 10 of FIGS. 1-3. The medical instrument holding platform 130 has a textured surface 140 that is created from removing at least a portion of the top surface 132 of the medical instrument holding platform 130. For example, the top surface 132 may be subjected to an abrasive compound, such as a particulate that is directed at a high velocity to the surface 132 of the medical instrument holding platform 130. The particulate may be a sand material, an organic material, or an inorganic material. Accordingly, the textured surface 140 may be formed below the top surface 132 of the medical instrument holding platform 130 after it is subjected to the abrasive compound.

Figure 5:
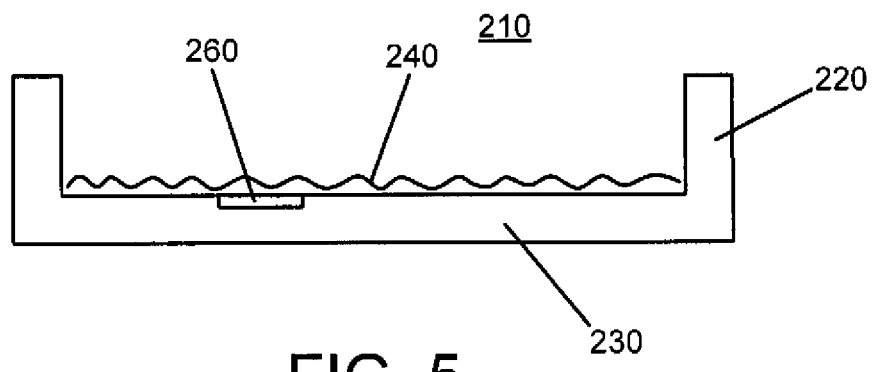
FIG. 5 is a side cross-sectional view illustration of a medical instrument holding apparatus, in accordance with a third exemplary embodiment of the present disclosure.

FIG. 5 is a side cross-sectional view illustration of a medical instrument holding apparatus 210, in accordance with a third exemplary embodiment of the present disclosure. The medical instrument holding apparatus 210, which may be referred to as 'apparatus 210,' may be substantially similar to the apparatuses of FIGS. 1-4. The apparatus 210 includes a medical instrument container 220. A medical instrument holding platform 230 is positioned within the medical instrument container 220, wherein the medical instrument holding platform 230 has a textured surface 240. At least one textual or graphic marking 260 is positioned on the textured surface 240. As is shown in FIG. 5, the medical instrument holding platform 230 is integrally formed with the medical instrument container 220, such that the medical instrument holding platform 230 is at least a portion of the base of the medical instrument container 220. The textured surface 240 and the textual or graphical markings 260 may be positioned on the medical instrument holding platform 230 formed with the base of the medical instrument container 220.

Figure 6:
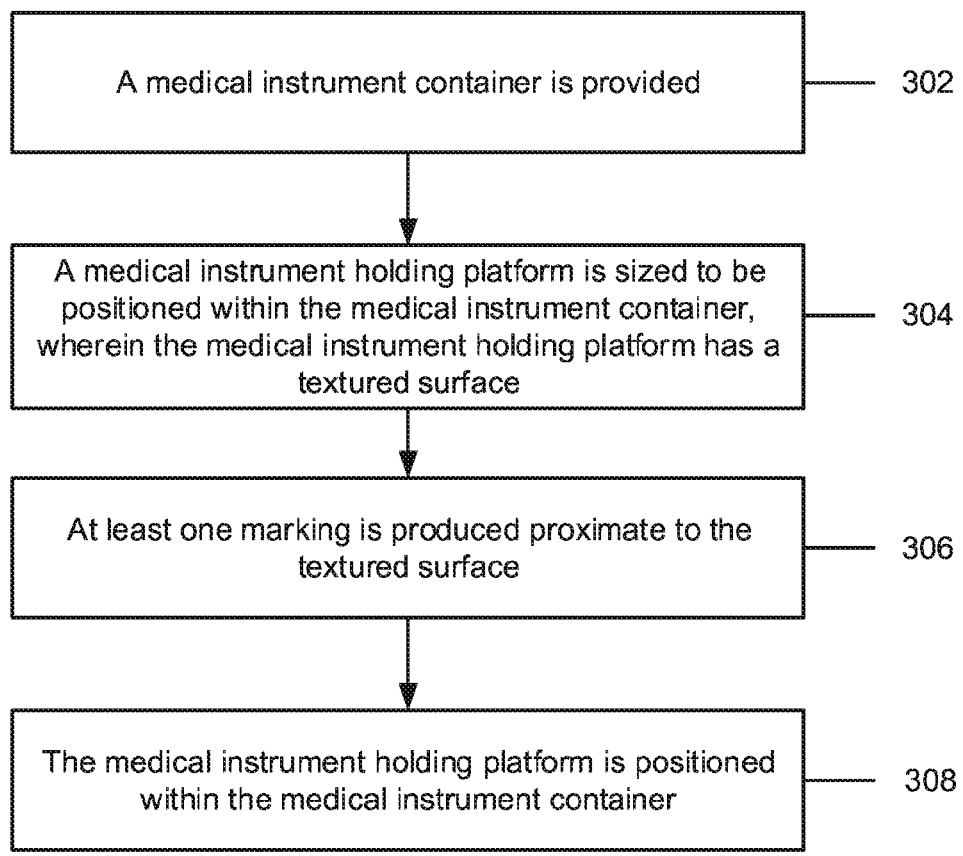
FIG. 6 is a flowchart illustrating a method of manufacturing a medical instrument holding apparatus, in accordance with a fourth exemplary embodiment of the disclosure.

FIG. 6 is a flowchart 300 illustrating a method of manufacturing a medical instrument holding apparatus, in accordance with a fourth exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 302, a medical instrument container is provided. A medical instrument holding platform is sized to be positioned within the medical instrument container, wherein the medical instrument holding platform has a textured surface (block 304). At least one marking is produced proximate to the textured surface (block 306). The medical instrument holding platform is positioned within the medical instrument container (block 308). The method may include any additional number of steps, processes, functions or variations thereof, including any of the steps, processes, and functions disclosed with respect to FIGS. 1-5. For example, in manufacturing the medical instrument holding platform, a molding or a texturing process may be used. The molding process may include molding the medical instrument holding platform with the textured surface therein, such that when the medical instrument holding platform is removed from the mold, the textured surface is formed on the medical instrument holding platform. The molding process, for example, may be an injection molding process.

When a texturing process is used, the medical instrument holding platform may be manufactured without the textured surface and then be subjected to a process for removing a portion of the surface of the medical instrument holding platform, thereby forming the textured surface. This process may include, for example, subjecting the medical instrument holding platform to an abrasive compound, such as a particulate that is directed at a high velocity to the surface of the medical instrument holding platform. The particulate may be a sand material, an organic material, or an inorganic material. It is noted that the textured surface of the medical instrument holding platform is not created by adding any material or substance to the medical instrument holding platform, but only by forming the medical instrument holding platform with the textured surface therein, or removing material from the medical instrument holding platform to form the textured surface.

Figure 7:
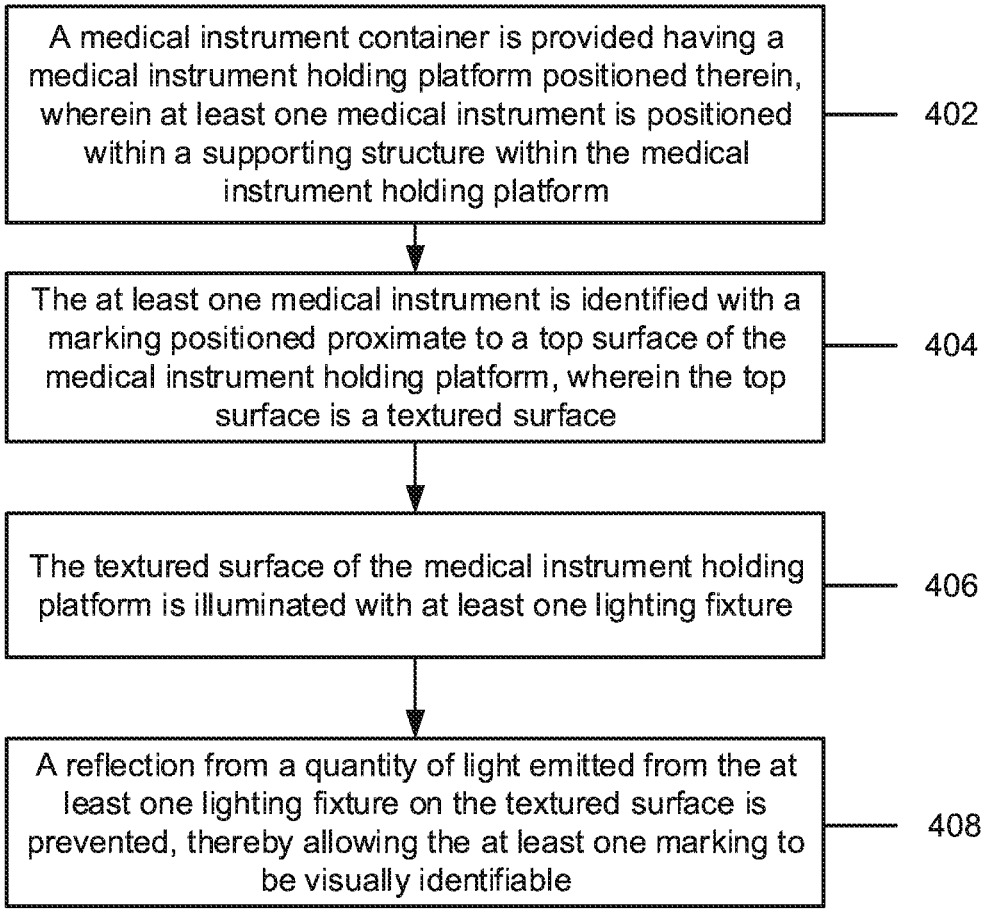
FIG. 7 is a flowchart illustrating a method of using a medical instrument holding apparatus within a medical operation setting, in accordance with a fifth exemplary embodiment of the disclosure.

FIG. 7 is a flowchart 400 illustrating a method of using a medical instrument holding apparatus within a medical operation setting, in accordance with a fifth exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 402, a medical instrument container is provided having a medical instrument holding platform positioned therein, wherein at least one medical instrument is positioned within a supporting structure within the medical instrument holding platform. The at least one medical instrument is identified with a marking positioned proximate to a top surface of the medical instrument holding platform, wherein the top surface is a textured surface (block 404). The textured surface of the medical instrument holding platform is illuminated with at least one lighting fixture (block 406). A reflection from a quantity of light emitted from the at least one lighting fixture on the textured surface is prevented, thereby allowing the at least one marking to be visually identifiable (block 408).

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claim.

What is claimed is:

1. A medical instrument holding apparatus adapted to hold medical devices during a sterilization process, the apparatus comprising:
   a medical instrument container having a plurality of upwardly extending sidewalls;
   a medical instrument holding platform configured to be positioned within the medical instrument container and interior to the plurality of upwardly extending sidewalls, wherein the medical instrument holding platform is comprised of:

a first material; and
a second material disposed within the first material and of different material composition from the first material, wherein the second material provides the medical instrument holding platform with a textured surface comprising a plurality of textural features having a size of 1,000 µm or less; and
at least one marking positioned on the textured surface of the medical instrument holding platform;
wherein:
the medical instrument holding apparatus is of a material construction capable of withstanding the sterilization process; and
the sterilization process is selected from a high-temperature sterilization process and a chemical sterilant-based sterilization process.

2. The medical instrument holding apparatus of claim 1, wherein the at least one marking comprises at least one of a textual marking and a graphical marking.

3. The medical instrument holding apparatus of claim 1, wherein the at least one marking comprises a laser-etched marking.

4. The medical instrument holding apparatus of claim 1, wherein the at least one marking comprises an ink-based marking.

5. The medical instrument holding apparatus of claim 1, wherein the at least one marking is positioned below the textured surface and is visible through the textured surface.

6. The medical instrument holding apparatus of claim 1, further comprising a medical instrument, wherein the at least one marking is positioned proximate to an instrument supporting structure on the medical instrument holding platform, wherein the at least one marking identifies a characteristic of the medical instrument, wherein the medical instrument is received within the instrument supporting structure.

7. The medical instrument holding apparatus of claim 1, wherein the textured surface is free from an added texturing material affixed to the medical instrument holding platform after it is constructed.

8. The medical instrument holding apparatus of claim 1, wherein the textured surface includes at least one of bumps and ridges.

9. The medical instrument holding apparatus of claim 1, wherein the medical instrument holding platform forms at least one of a base and a cover of the medical instrument container.

10. The medical instrument holding apparatus of claim 1, wherein each of the container and the platform include a material selected from: polyphenylsulfone, polyetherimide, polyethersulfone, and polypropylene.

11. The medical instrument holding apparatus of claim 1, wherein the textured surface has a light reflectance value of less than 50% for ambient room lighting.

12. The medical instrument holding apparatus of claim 11, wherein the textured surface has a light reflectance value of less than 40% for ambient room lighting.

13. The medical instrument holding apparatus of claim 12, wherein the textured surface has a light reflectance value of less than 20% for ambient room lighting.

14. The medical instrument holding apparatus of claim 1, further comprising a lid adapted to be supported by the plurality of upwardly extending sidewalls.

15. The medical instrument holding apparatus of claim 1, wherein the medical instrument holding platform is permanently affixed to the medical instrument container.

16. The medical instrument holding apparatus of claim 1, wherein the medical instrument holding platform is removably affixed to the medical instrument container.

17. The medical instrument holding apparatus of claim 1, wherein the second material includes at least one of a granular material, a glass fiber and a carbon fiber.

18. A medical instrument holding apparatus adapted to hold medical devices during a sterilization process, the apparatus comprising:
a medical instrument container having a plurality of upwardly extending sidewalls;
a medical instrument holding platform configured to be positioned within the medical instrument container and interior to the plurality of upwardly extending sidewalls, wherein the medical instrument holding platform has a textured surface created by removal of at least a portion of a top surface of the medical instrument holding platform, the textured surface comprising a plurality of textural features having a size of 1,000 µm or less; and
at least one marking positioned on the textured surface of the medical instrument holding platform;
wherein:
the medical instrument holding apparatus is of a material construction capable of withstanding the sterilization process; and
the sterilization process is selected from a high-temperature sterilization process and a chemical sterilant-based sterilization process.

19. The medical instrument holding apparatus of claim 18, wherein the textural features have a size of 500 µm or less.

20. The medical instrument holding apparatus of claim 1, wherein the textural features have a size of 500 µm or less.

* * * * *